United States Patent [19]
Phillipps

[11] 3,982,528
[45] Sept. 28, 1976

[54] APPARATUS FOR REFINING SIGNALS DERIVED FROM FETAL HEARTBEATS

[75] Inventor: Patrick G. Phillipps, Newton, Mass.

[73] Assignee: Brattle Instrument Corporation, Cambridge, Mass.

[22] Filed: Feb. 24, 1975

[21] Appl. No.: 552,233

[52] U.S. Cl. .................. 128/2.05 T; 128/2.05 Z; 235/181
[51] Int. Cl.² .......................................... A61B 5/02
[58] Field of Search ............... 128/2.05 P, 2.05 Q, 128/2.05 R, 2.05 S, 2.05 T, 2.05 V, 2.05 Z, 2.06 A, 2.06 F, 2.06 G, 2.06 R, 2.1 R; 235/181

[56] References Cited
UNITED STATES PATENTS

| | | | |
|---|---|---|---|
| 2,840,308 | 6/1958 | Van Horne | 235/181 |
| 3,185,958 | 5/1965 | Masterson et al. | 235/181 |
| 3,646,333 | 2/1972 | Pryor, Jr. | 235/181 |
| 3,717,756 | 2/1973 | Stitt | 235/181 |
| 3,780,725 | 12/1973 | Goldberg | 128/2.05 T |
| 3,811,428 | 5/1974 | Van Horn et al. | 128/2.06 F |

Primary Examiner—William E. Kamm

[57] ABSTRACT

Circuitry for refinement of fetal heart signals from an ultrasonic (or other mechanical energy) transducer, featuring improved signal processing circuitry connected to the transducer to convert useful information-carrying energy in the transducer output into a refined electrical signal, and improved correlation circuitry for providing an output to a cardiotachometer.

15 Claims, 15 Drawing Figures

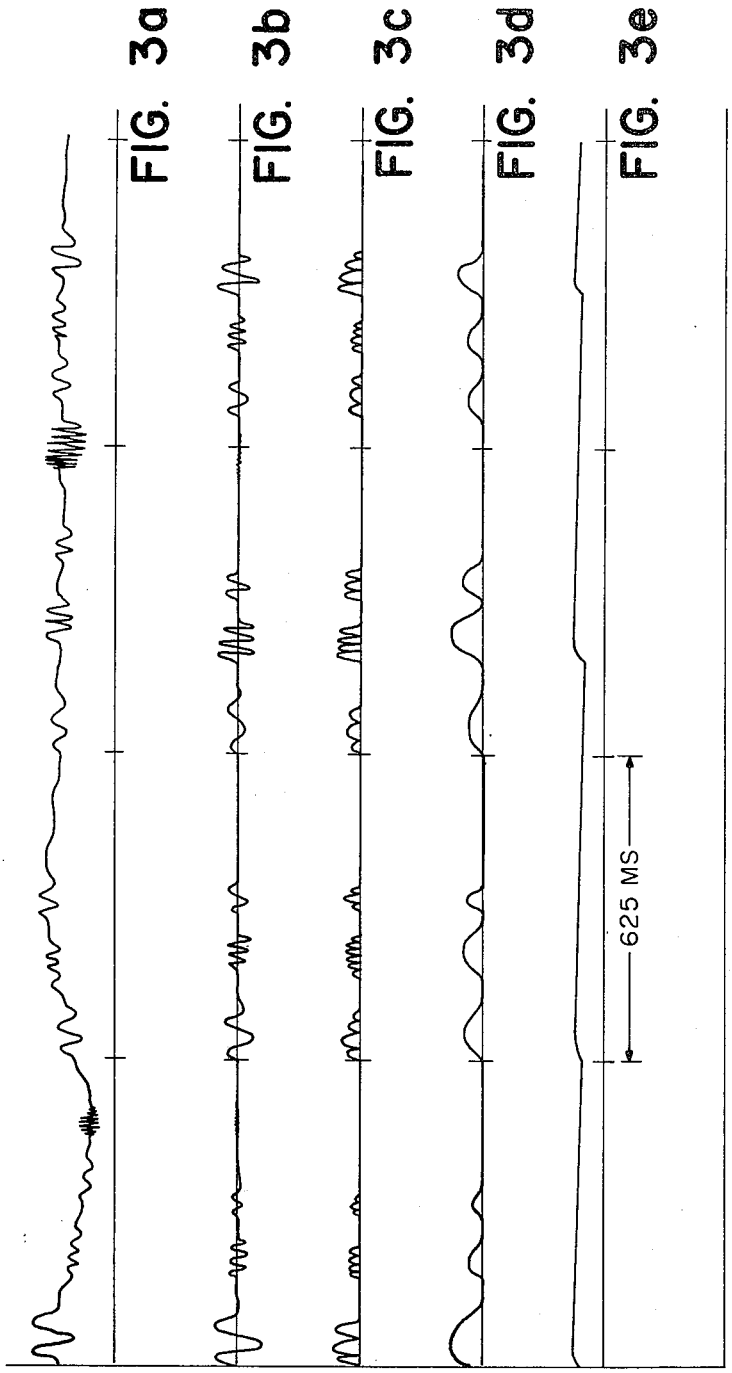

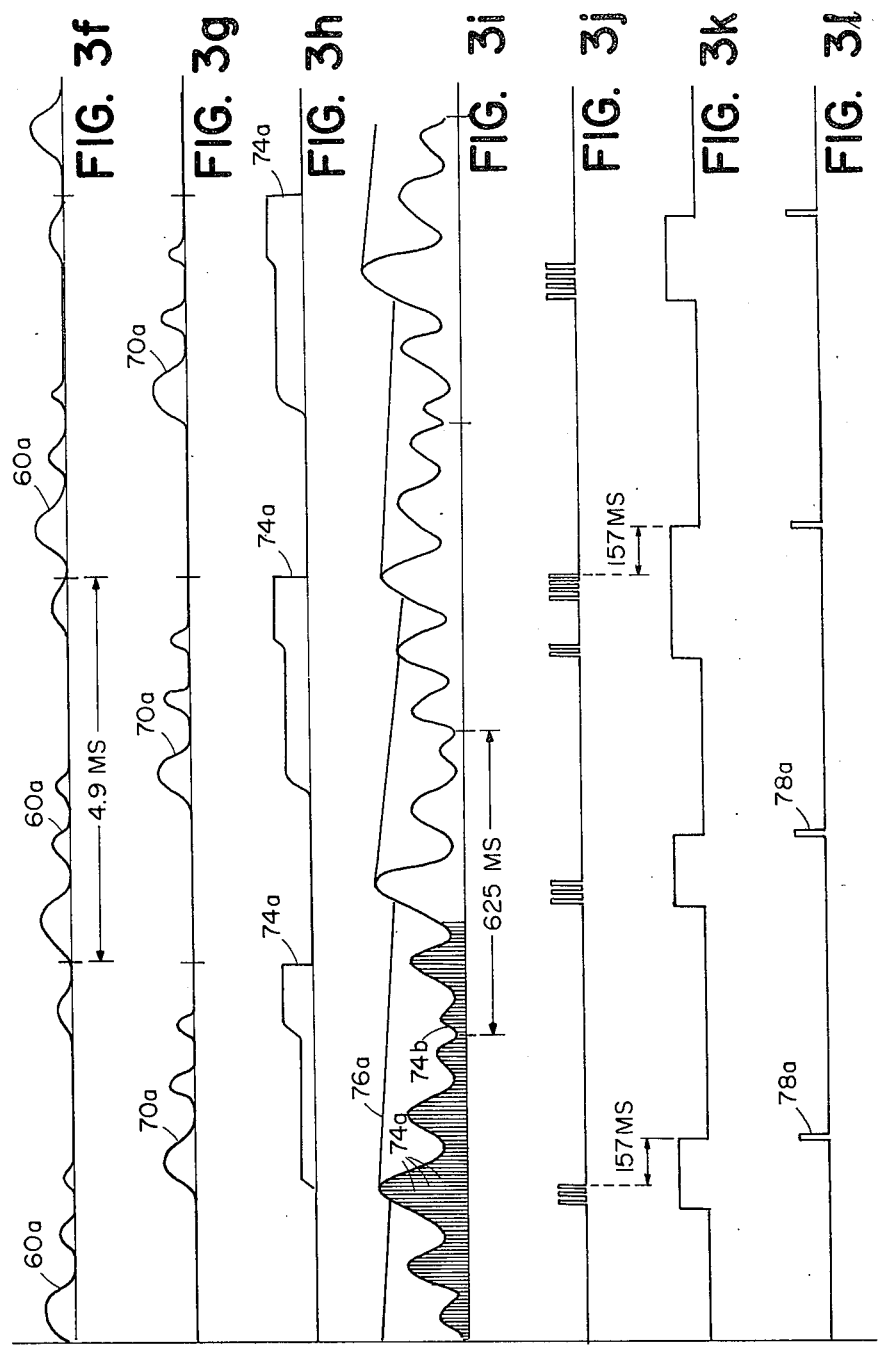

APPARATUS FOR REFINING SIGNALS DERIVED FROM FETAL HEARTBEATS

BACKGROUND OF THE INVENTION

This invention relates to monitoring the fetal heart cycle.

A tachometer useful for deriving a fetal heart rate from an electrical signal impressed with the fetal heart cycle is disclosed in U.S. Pat. No. 3,811,428.

At times it is desirable to use such a tachometer with an input signal derived from the fetal heart cycle through a mechanical energy transducer, such as an ultrasonic or phonocardiographic pickup. Problems in obtaining good quality inputs from such pickups have been experienced.

SUMMARY OF THE INVENTION

The invention provides improved circuitry for refinement of fetal heart signals from an ultrasonic (or other mechanical energy) transducer. High signal quality is achieved with inexpensive components despite the highly stochastic nature and unpredictable location of the signal elements being detected. Clinical use is simple, convenient (e.g., precise aiming of a narrow ultrasonic beam is not required), and safe. The data dropout rate is extremely low.

In one aspect the invention features a transducer for converting mechanical energy impressed with the fetal heart cycle into a raw electrical signal including energy carrying information related to the cycle, signal processing circuitry means connected to the transducer to convert the information-carrying energy into a refined electrical signal, the circuitry including amplitude normalizing means to cause the refined electricl signal to trace amplitude variations in the energy relative to the currently prevailing average level of the energy, correlation circuitry means connected to the signal processing circuitry means including first means for storing portions of the refined signal corresponding to successive current fetal heart cycles and second means for forming and storing a sample signal derived from portions of the refined signal corresponding to one or more previous fetal heart cycles, and third means for forming the correlation function in time between the signals stored in the first and second means, and output circuitry means for detecting successive peaks of the correlation function corresponding to successive fetal heart cycles and providing an output signal based upon the occurrences of the peaks. In another aspect the invention features signal processing circuitry means including the combination of an absolute value circuit and a low pass filter for narrowing the bandwidth of the refined signal. In yet another aspect the invention features digital correlation circuitry including digital signal and sample registers respectively arranged as delay line time compression circuits, the sample register being connected to the output circuitry for modifying the stored sample signal, upon detection of the peak of the correlation function, by averaging the stored sample with the refined signal corresponding to the heart cycle for which the peak was detected, and storing the modified sample, means being provided to recirculate the data in the registers once for each word received by the correlation circuitry, and for causing precession of the data in the registers, a digital adder and a delay register being connected between the signal and sample registers for compensating, prior to the averaging, for the misalignment, due to the precession, between the stored sample and the signal to be averaged therewith. In yet another aspect the invention features output circuitry including delay means for providing the output signal only after a peak-free delay of predetermined length (preferably 15% to 35% of the predicted average period of the heart cycle being measured and at least 100 milliseconds) following the detection of a correlation function peak. In yet another aspect the invention features means (preferably in the form of a monostable delay) for limiting the frequency of the sample averaging. In yet another aspect the invention features output circuitry including signal quality evaluation means connected to the correlation circuitry means to inhibits operation of the correlation circuitry means to allow the refined signals to pass directly to the output circuitry in the event the output circuitry means fails to detect a new peak of the correlation function for a predetermined length of time. In preferred embodiments the amplitude normalizing means includes peak detector means for providing a decaying reference signal derived from peaks in the information-carrying energy, and means connected to the peak detector for providing as the refined signal the ratios of successive amplitude levels of the energy to the reference signal; the last-mentioned means comprises analog to digital converter means for repeatedly sampling the amplitude level of the energy and providing as the refined signal digital outputs corresponding to the ratios of said sampled levels to the reference signal; the transducer is an ultrasonic transducer including a transmitter and a receiver; and audio output circuitry is connected to the signal processing circuitry.

Other advantages and features of the invention will appear from the following description of a preferred embodiment thereof, including the drawings.

BRIEF DESCRIPTION OF THE DRAWINGS

FIGS. 3a through 3l are illustrations of signal forms at different points in the circuitry of FIGS. 2a and 2b.

DESCRIPTION OF THE PREFERRED EMBODIMENT

Figure 1:
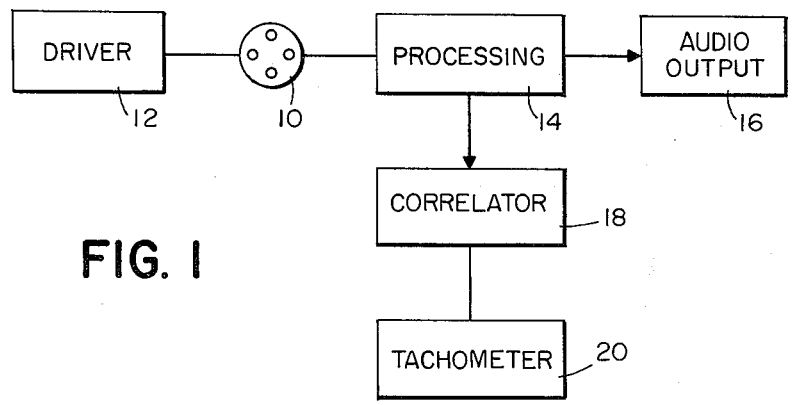
FIG. 1 is an overall block diagram of the invention.
Figure 2A:
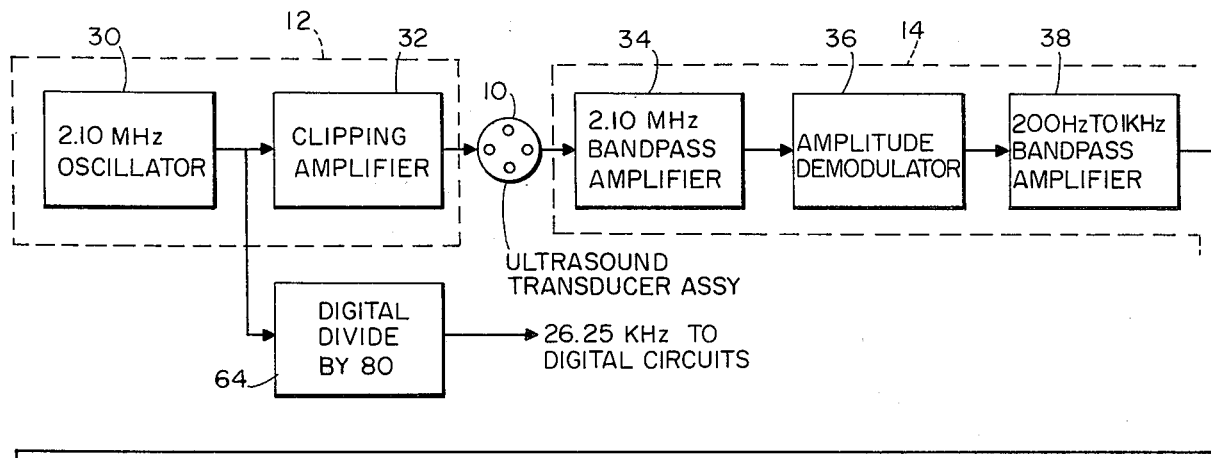
FIGS. 2a and 2b are more detailed block diagrams of the circuitry of FIG. 1.
Figure 2A:
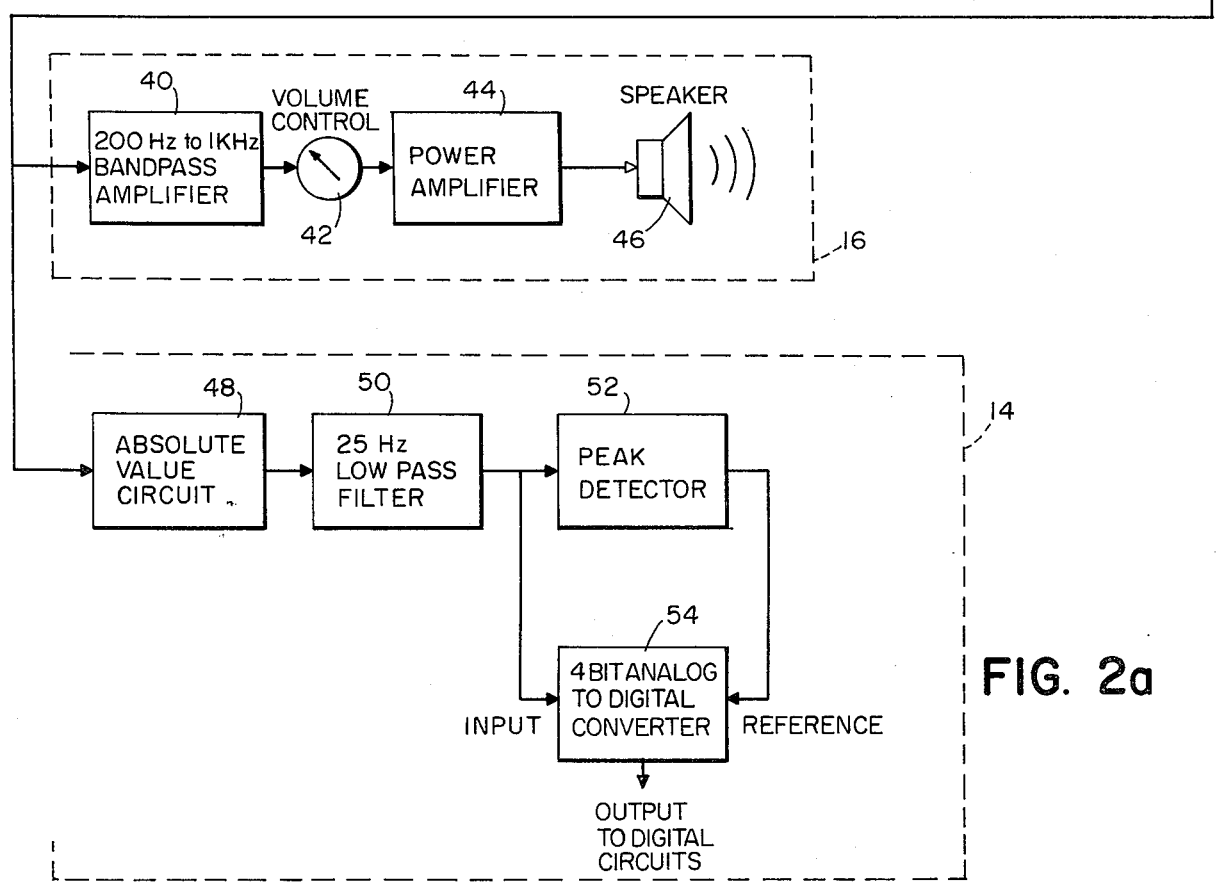
Figure 2B:
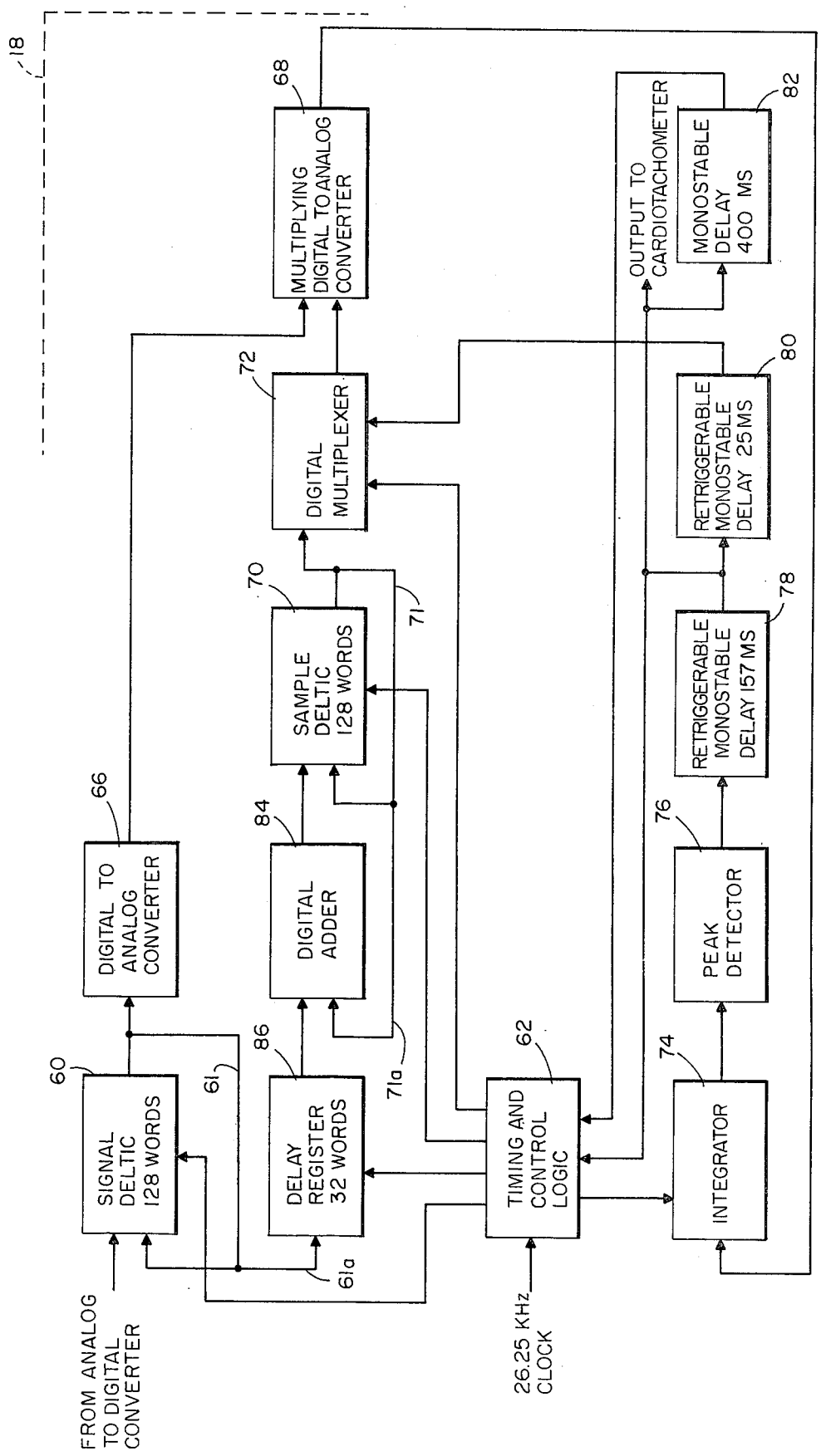

As shown in FIG. 1, the overall system includes an ultrasonic transducer 10 activated by transducer driver circuitry 12, processing circuitry 14 for processing the output of transducer 10, audio output 16 which receives analog signals from circuitry 14, and correlation circuitry 18 which receives from circuitry 14 and processes digital signals and in turn feeds cardiotachometer 20.

Driver circuitry 12 consists of 2.10 MHz oscillator 30, the sinusoidal output of which is clipped by amplifier 32 to provide a highly stable, standardized signal of 10 volts peak to peak amplitude. Transducer 10 is positioned on the patient to beam 2.10 MHz ultrasonic energy into the uterus, and to receive the ultrasound signal reflected from the body surfaces including the fetal heart. The reflected signal is converted into an electrical signal which is amplified by 2.10 MHz bandpass amplifier 34 and demodulated by amplitude demodulator 36 to produce a signal of the general character illustrated in FIG. 3a. In particular, it has been discovered that, apparently due to doppler frequency shift in the ultrasound signal reflected from the moving fetal heart walls and valves, the output of demodulator 36 contains periodic energy in the 200 Hz to 1 KHz band width which is usefully related to the fetal cardiac cycle. Accordingly, the output of demodulator 36 is filtered and amplified by 200 Hz to 1 KHz bandpass amplifier 38. Amplifier 38 feeds audio output 16 (which includes a second 200 Hz to 1 KHz bandpass amplifier 40, volume control 32, power amplifier 44, and speaker 46), as well as absolute value circuitry 48. The signal from amplifier 38 is illustrated in FIG. 3b, and that from circuitry 48 (a positive signal proportional to the magnitude of the demodulator output) is illustrated in FIG. 3c. After removal of further high frequency noise by 25 Hz (preferred range 15–50 Hz) low pass filter 50, producing the signal illustrated in FIG. 3d, the signal is fed to peak detector 52 and 4 bit analog to digital converter 54. Peak detector 52 provides to converter 54 a reference voltage which decays exponentially from the most recently detected peak received from filter 50. Converter 54 samples the signal from filter 50 every 4.9 milliseconds and divides that sample by the current reference voltage from detector 52 to provide a succession of 4 bit digital outputs which effectively trace the variations in the filtered signal amplitude relative to the currently prevailing average signal level.

The amplitude normalization provided by peak detector 52 and converter 54 makes possible accurate digital representation and processing of the cardiac cycle related information with only four bits per word, and the signal bandwidth narrowing accomplished by the combination of absolute value circuitry 48 and low pass filter 50 minimizes the length of the memory registers required.

Correlation circuitry 18 includes a delay line time compression circuit (deltic) 60 consisting of four parallel 128 bit shift registers which receive a new output word from converter 54 each 4.9 milliseconds. Signal deltic 60 thus contains at any given time information describing the output of converter 54 for the previous 625 milliseconds, which is the predicted average duration of the heart cycle being measured. The data in deltic 60 is completely recirculated in the deltic once for each new word of data received, i.e., once each 4.9 milliseconds. This and other control functions of the correlator circuitry are governed by suitable time and control logic 62 which is driven by a 26.25 KHz signal obtained from driver circuitry 12 through digital divide by 80 circuitry 64 and provides a clock signal to shift the data in deltic 60 one bit every 38 microseconds. Data from deltic 60 passes, one word each 38 microseconds, to digital to analog converter 66 which provides to multiplying digital to analog converter 68 a time compressed normalized amplitude version of the output of filter 50. Sample deltic 70, identical to deltic 60, in general stores a sample formed by averaging successive sets of data corresponding approximately to successive heart cycles, respectively.

Each deltic 60, 70 has a recirculation line 61, 71 through which the data stored in the deltic is recirculated at a recirculation rate of one word each 38 microseconds. One shifting clock pulse to sample deltic 70 is omitted each time a new word enters deltic 60, so that the data in deltic 70 will precess relative to that in deltic 60 one word for each complete recirculation (i.e., each 4.9 milliseconds).

The data from deltic 70 passes through digital multiplexer 72 to the second input to converter 68 in which word by word multiplication of the current signal and sample data occurs. The 128 word by word products are fed to integrator 74 where they are summed for each 4.9 millisecond interval, the integrator being reset every 4.9 milliseconds by logic 62. As will be apparent, data flow in the circuit from signal deltic 60 through integrator 74 is at the recirculation rate.

The output of integrator 74 each 4.9 milliseconds is proportional to the correlation of the data in deltic 60 to that in deltic 70, and because of the position of the sample data, successive peak values of the integrator output form the autocorrelation function in time between the data in the deltics. The outputs 60a and 70a, respectively of deltics 60 and 70 and the outputs 74a of integrator 74 for successive 4.9 millisecond intervals are respectively illustrated in FIGS. 3f, 3g, and 3h.

Peak detector 76 monitors the output of integrator 74 by comparing that output to a reference equal the gradually decaying value of the most recently detected peak. The decay occurs according to the relationship $V = V_o e^{-t/\lambda}$, where V=the decayed voltage, $V_o$=the detected peak voltage, t=time, and λ= a time constant (chosen to be one second in the embodiment being described) corresponding to the time necessary for 63% decay in the voltage level. The relationship of the peak detector tracking voltage 76a to the output 74a of integrator 74 is illustrated in FIG. 3i, each vertical line 74a under curve 74b corresponds to the summation output of integrator 74 for a 4.9 millisecond interval.

Each time peak detector 76 detects a new peak, it triggers retriggerable monostable delay 78 (the triggering being illustrated in FIG. 3j), which, after a peak-free delay of 157 milliseconds from the last triggering, provides an output pulse (FIGS. 3k and 3l) to the cardiotachometer. The calibration of the time constant of peak detector 76 and the delay time of one shot 78 are chosen to avoid multiple output pulses for a single heart cycle, while permitting detection of the actual peak in each cycle. In particular, the delay in one shot 78 should be in the range of 15% to 35% of the predicted average period of the heart cycle being measured, and should be at least 100 milliseconds.

It has been found that the time between pulses 78a from delay 78 accurately measured the instantaneous fetal heart period being measured.

Pulses 78a are also fed to retriggerable monostable delay 80, monostable delay 82, and logic 62.

Delay 80 is connected to digital multiplexer 72 and inhibits operation of the correlator to allow the refined signals to pass directly to the output circuitry if detector 76 has not seen a new peak for 2 seconds. This is accomplished by causing the multiplexer to pass a single impulse in the center of the 4.9 millisecond cycle to converter 68 in place of the output of deltic 70. Once detector 76 sees a new peak the correlator resumes normal auto-correlation operation.

The receipt of a pulse 78a by logic 62 causes the contents of sample deltic 70 to be circulated through line 71a into digital adder 84 where they are averaged with corresponding data from deltic 60 provided to the adder through line 61a and a set of parallel 32 bit delay registers 86. The output of adder 84 is fed back to deltic 70 to provide a new sample. Delay 86 is needed to restore the data in deltic 70 to its original position relative to the data stream entering deltic 60, since when pulse 78a occurs the data in deltic 70 will have precessed 32 bits from its position at the time it was multiplied with the data in deltic 60 to produce the peak at integrator 74.

Delay 82 is connected to logic 62 to prevent replacement of the sample in deltic 70 more than once every 400 milliseconds.

Examples of semiconductor chips useful in the circuitry described above are:

| | |
|---|---|
| Amplifiers 38 and 40, absolute value circuitry 48, low pass filter 50, and peak detector 52 | National Semiconductor LM 741C |
| Divide by 80 circuitry 64 | Texas Instruments SN 7490N and SN 7493N |
| Transducer 10 | Hewlett Packard Model 15155A |
| Amplifier 44 | National Semiconductor LM 380 |
| Converter 54 | Texas Instruments SN 74191, Motorola MC 1406, and National Semiconductor LM 311 |
| Converter 66 and peak detector 76 | National Semiconductor LM 741 |
| Deltics 60 and 70 | National Semiconductor MM 5055 |
| Delay 86 | Signetics 2418 |
| Adder 84 | Texas Instruments SN 7483A |
| Multiplexer 72 | Texas Instruments SN 74157 |
| Converter 68 | Motorola MC 1406 |
| Integrator 74 | National Semiconductor LM 741 and Intersil IH 5004 |
| Delays 78, 80 and 82 | Texas Instruments SN 74123 |

Oscillator 30, clipping amplifier 32, bandpass amplifier 34 and demodulator 36 are conventional circuits, of the general sort described, e.g., in Radio Amateurs Handbook (American Radio Relay League, 1973) at pages 139, 447, 266, and 237, respectively.

Logic and control circuitry 62 employs conventional circuitry design for carrying out the functions described.

Other embodiments are within the following claims:

I claim:

1. A device for providing a periodic electrical output derived from fetal heartbeats, comprising
   a transducer for converting mechanical energy impressed with the fetal heart cycle into a raw electrical signal including energy carrying information related to said cycle,
   signal processing circuitry means connected to said transducer to convert said information-carrying energy into a refined electrical signal,
   correlation circuitry means connected to said signal processing circuitry means including first means for storing portions of said refined signal corresponding to successive current fetal heart cycles and second means for forming and storing a sample signal derived from portions of said refined signal corresponding to one or more previous fetal heart cycles, and third means for forming the correlation function in time between the signals stored in said first and second means, and
   output circuitry means for detecting successive peaks of said correlation function corresponding to successive fetal heart cycles and providing an output signal based upon the occurrences of said peaks,
   said output circuitry means including peak detector means for comparing the value of said correlation function to a reference related to the value of the most recently detected peak of said function, and delay means for providing said output signal only after a peak-free delay of predetermined length following the detection of a peak of said correlation function.

2. The device of claim 1 wherein the length of said delay is 15%–35% of the predicted average period of the heart cycle being measured.

3. The device of claim 2 wherein said delay is at least 100 milliseconds.

4. The device of claim 1 wherein said delay means comprises a retriggerable monostable delay.

5. The device of claim 1 wherein said signal processing circuitry means includes amplitude normalizing means to cause said refined electrical signal to trace amplitude variations in said energy relative to the currently prevailing average level of said energy.

6. The device of claim 5 wherein said amplitude normalizing means includes peak detector means for providing a decaying reference signal derived from peaks in said information carrying energy, and means connected to said peak detector for providing as said refined signal the ratios of successive amplitude levels of said energy to said reference signal.

7. The device of claim 6 wherein said last mentioned means comprises analog to digital converter means for repeatedly sampling said amplitude level of said energy and providing as said refined signal digital outputs corresponding to the ratios of said sampled levels to said reference signal.

8. The device of claim 1 wherein said second means comprises means connected to said output circuitry for modifying said stored sample signal, upon detection of a peak of said correlation function, by averaging said stored sample with the refined signal corresponding to the heart cycle for which said peak was detected, and storing said modified sample.

9. The device of claim 8 wherein said third means includes digital means for providing to said correlation circuitry means said refined signal as a succession of digital words, said first and second means comprising digital signal and sample registers, respectively, arranged as delay line time compression circuits, means being provided for recirculating the data in said registers at a recirculation rate sufficiently faster than the data rate at which said words are received by said correlation circuitry means so as to completely recirculate said data in said registers once for each said word received by said correlation circuitry, means being provided for causing said data in said sample register to precess relative to said data in said signal register,
   said means connected to said output circuitry means including digital adder means connected in series with said sample register for carrying out said averaging and delay register means connected between said signal register and said sample register for compensating, prior to said averaging, for the misalignment, due to said precession, between said stored sample and said signal to be averaged therewith.

10. The device of claim 1 wherein said transducer is an ultrasonic transducer including a transmitter and a receiver.

11. The device of claim 1 further comprising audio output circuitry means connected to said processing circuitry means, 12. The device of claim 1 wherein said signal processing circuitry means includes the combination of an absolute value circuit and a low pass filter for narrowing the bandwidth of said refined signal.

13. The device of claim 12 wherein said low pass filter has a cutoff frequency of between 15 and 50 Hz.

14. A device for providing a periodic electrical output derived from fetal heartbeats, comprising
a transducer for converting mechanical energy impressed with the fetal heart cycle into a raw electrical signal including energy carrying information related to said cycle,
signal processing circuitry means connected to said transducer to convert said information-carrying energy into a refined electrical signal,
correlation circuitry means connected to said signal processing circuitry means including first means for storing portions of said refined signal corresponding to successive current fetal heart cycles and second means for forming and storing a sample signal derived from portions of said refined signal corresponding to one or more previous fetal heart cycles, and third means for forming the correlation function in time between the signals stored in said first and second means, and
output circuitry means for detecting successive peaks of said correlation function corresponding to successive fetal heart cycles and providing an output signal based upon the occurrences of said peaks,
said second means comprising means connected to said output circuitry for modifying said stored sample signal, upon detection of a peak of said correlation function, by averaging said stored sample with the refined signal corresponding to the heart cycle for which said peak was detected, and storing said modified sample,
said device further comprising means connected between said output circuitry and said means for modifying said stored sample, for limiting the frequency of said averaging,
said means for limiting comprising a monostable delay.

15. A device for providing a periodic electrical output derived from fetal heartbeats, comprising
a transducer for converting mechanical energy impressed with the fetal heart cycle into a raw electrical signal including energy carrying information related to said cycle,
signal processing circuitry means connected to said transducer to convert said information-carrying energy into a refined electrical signal,
correlation circuitry means connected to said signal processing circuitry means including first means for storing portions of said refined signal corresponding to successive current fetal heart cycles and second means for forming and storing a sample signal derived from portions of said refined signal corresponding to one or more previous fetal heart cycles, and third means for forming the correlation function in time between the signals stored in said first and second means, and
output circuitry means for detecting successive peaks of said correlation function corresponding to successive fetal heart cycles and providing an output signal based upon the occurrences of said peaks,
said output circuitry means including signal quality evaluation means connected to said correlation circuitry means to inhibit operation of said correlation circuitry means to allow said refined signals to pass directly to said output circuitry in the event said output circuitry means fails to detect a new peak of said correlation function for a predetermined length of time.

* * * * *